United States Patent
Toyoda et al.

(10) Patent No.: US 10,940,253 B2
(45) Date of Patent: Mar. 9, 2021

(54) BLOOD PURIFICATION APPARATUS

(71) Applicant: Nikkiso Company Limited, Tokyo (JP)

(72) Inventors: Masahiro Toyoda, Shizuoka (JP); Akira Sugioka, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 688 days.

(21) Appl. No.: 15/697,887

(22) Filed: Sep. 7, 2017

(65) Prior Publication Data

US 2017/0361004 A1 Dec. 21, 2017

Related U.S. Application Data

(63) Continuation of application No. PCT/JP2016/057502, filed on Mar. 10, 2016.

(30) Foreign Application Priority Data

Mar. 10, 2015 (JP) .............................. JP2015-047040

(51) Int. Cl.
*A61M 1/14* (2006.01)
*A61M 1/36* (2006.01)
*A61M 1/16* (2006.01)

(52) U.S. Cl.
CPC ............ *A61M 1/14* (2013.01); *A61M 1/1682* (2014.02); *A61M 1/365* (2014.02);
(Continued)

(58) Field of Classification Search
CPC .................. A61M 1/14; A61M 1/3656; A61M 2205/3306; A61M 2205/3334; A61M 1/365; A61M 1/3653
See application file for complete search history.

(56) References Cited

U.S. PATENT DOCUMENTS 5,863,421 A * 1/1999 Peter, Jr. ................... A61L 2/04
210/134
7,147,616 B2 12/2006 Pedrazzi et al.
(Continued)

FOREIGN PATENT DOCUMENTS

JP H06-047090 2/1994
JP 2003-519539 6/2003
(Continued)

OTHER PUBLICATIONS

International Search Report from the Japanese Patent Office for Application No. PCT/JP2016/057502 dated May 31, 2016.
(Continued)

*Primary Examiner* — Leslie R Deak
(74) *Attorney, Agent, or Firm* — Young Basile Hanlon & MacFarlane, P.C.

(57) ABSTRACT

A blood purification apparatus where neither an arterial puncture needle nor a venous puncture needle is stuck in the patient can be checked automatically when it is attempted to activate a blood pump in an unconnected step. A blood purification apparatus includes a blood circuit for circulating blood, a dialyzer for purifying the blood, a blood pump provided to an arterial blood circuit for delivering liquid when activated, and a control device that executes a connected step when blood pump is activated with an arterial puncture needle (a) and a venous puncture needle (b) being stuck in the patient and an unconnected step in which the blood pump is activated with neither the arterial puncture needle (a) nor the venous puncture needle (b) being stuck in the patient.

20 Claims, 9 Drawing Sheets

(52) U.S. Cl.
CPC ........ *A61M 1/3646* (2014.02); *A61M 1/3652* (2014.02); *A61M 1/3653* (2013.01); *A61M 1/3656* (2014.02); *A61M 2205/276* (2013.01); *A61M 2205/331* (2013.01); *A61M 2205/3306* (2013.01); *A61M 2205/3334* (2013.01)

(56) References Cited

U.S. PATENT DOCUMENTS

| | | | |
|---|---|---|---|
| 7,959,593 B2* | 6/2011 | Ueda .................. | A61M 1/3643 604/6.09 |
| 2003/0100857 A1 | 5/2003 | Pedrazzi et al. | |
| 2007/0118064 A1 | 5/2007 | Ueda et al. | |
| 2013/0020237 A1 | 1/2013 | Wilt et al. | |
| 2013/0030347 A1* | 1/2013 | Sugioka .............. | A61M 1/3465 604/6.09 |
| 2016/0095971 A1* | 4/2016 | Kopperschmidt .. | A61M 1/3639 604/4.01 |

FOREIGN PATENT DOCUMENTS

| | | |
|---|---|---|
| JP | 2007-020962 | 2/2007 |
| JP | 2007-135885 | 6/2007 |
| JP | 2010-136841 | 6/2010 |
| JP | 2010-184029 | 8/2010 |
| WO | 2001/051106 | 7/2001 |

OTHER PUBLICATIONS

International Search Report from the Japanese Patent Office for Application No. PCT/JP2016/057501 dated Jun. 7, 2016.
Co-pending U.S. Appl. No. 15/697,873, filed Sep. 7, 2017.
Extended European Search Report from the European Patent Office for Application No. PCT/JP2016/057502, dated Aug. 27, 2018.

* cited by examiner

(*1) Unconnected step (S1) Is circuit attached to blood-checking devices?

(S2) Activate ultrafiltration pump, and activate blood pump at low speed or keep blood pump stopped (S3) Has either of blood-cheking devices detected blood? (checking step)

(S4) Prohibit activation of blood pump (S5) Give notification

(S6) Predetermined time period or predetermined flow rate?

(S7) Operate blood pump at predetermined flow rate (S8) Prohibit activation of blood pump (S9) Give notification

[ Fig 3 ]

(∗1) Unconnected step (S1) Is circuit attached to blood-checking devices?

(S2) Active blood pump at low speed (S3) Has venous pressure risen? (checking step)

(S4) Operate blood pump at predetermined flow rate

(S5) Prohibit activation of blood pump (S6) Give notification (S7) Prohibit activation of blood pump (S8) Give notification

[Fig 4]

(*1) Unconnected step (S1) Is circuit attached to blood-checking devices?

(S2) Store blood concentrations (S3) Activate ultrafiltration pump,
    and activate blood pump at low speed or keep blood pump stopped (S4) Have blood concentrations risen? (checking step)

(S5) Prohibit activation of blood pump (S6) Give notification

(S7) Predetermined time period or predetermined flow rate?

(S8) Operate blood pump at predetermined flow rate (S9) Prohibit activation of blood pump

(S10) Give notification

BLOOD PURIFICATION APPARATUS

FIELD

The present teachings relate to a blood purification apparatus for purifying the blood of a patient while extracorporeally circulating the blood in a treatment such as a dialysis treatment performed by using a dialyzer.

BACKGROUND

In a general dialysis treatment, blood collected from a patient is extracorporeally circulated and is then returned to the body of the patient through a blood circuit. The blood circuit basically includes an arterial blood circuit and a venous blood circuit that are connectable to a dialyzer (a blood purification device) including, for example, hollow fiber membranes. The arterial blood circuit and the venous blood circuit are provided at the distal ends thereof with an arterial puncture needle and a venous puncture needle, respectively, which are stuck into the patient, whereby the blood is extracorporeally circulated through the blood circuit.

The arterial blood circuit is provided with a peristaltic blood pump. When the blood pump is activated with the arterial puncture needle and the venous puncture needle being stuck in the patient, blood collected from the body of the patient can be delivered into the dialyzer while being extracorporeally circulated. Usually, before a blood purification treatment is performed, some steps such as a priming step in which the blood circuit and so forth are filled with a priming solution are performed. Furthermore, after the blood purification treatment is performed, a returning step in which the blood in the blood circuit is returned into the patient is performed.

The dialyzer is provided with a dialysate introduction line through which dialysate is introduced into the dialyzer, and a dialysate drain line through which drain liquid is discharged from the dialyzer. After the returning step is performed, the arterial puncture needle and the venous puncture needle are removed from the patient. Then, the blood pump and associated devices are activated. Thus, a draining step in which liquid in the blood circuit is discharged into the dialysate drain line is performed (see PTL 1, for example). Through such a draining step, the liquid remaining in the blood circuit after the returning step can be disposed of easily

CITATION LIST

Patent Literature

PTL 1: Japanese Unexamined Patent Application Publication (Translation of PCT Application) No. 2003-519539 the teachings of which are expressly incorporated by reference herein for all purposes.

SUMMARY

The above blood purification apparatus has a possibility that, in the transition from the returning step to the draining step, the blood pump may be accidentally activated with, for example, the venous puncture needle being stuck in the patient. In particular, in the draining step, the blood pump and other associated devices are activated on the premise that neither the arterial puncture needle nor the venous puncture needle is stuck in the patient (an unconnected step). Therefore, monitoring in such a step is less strict than in other steps (connected steps) in which the blood pump is activated with the arterial puncture needle and the venous puncture needle being stuck in the patient. Consequently, no notification or the like may be issued even if the blood pump is activated with the arterial puncture needle or the venous puncture needle being stuck in the patient.

The present teachings have been conceived in view of the above circumstances and provides a blood purification apparatus in which the fact that neither an arterial puncture needle nor a venous puncture needle is stuck in the patient can be checked automatically when it is attempted to activate a blood pump in an unconnected step.

According to the teachings herein, there is provided a blood purification apparatus including a blood circuit including an arterial blood circuit to a distal end of which an arterial puncture needle is connectable, and a venous blood circuit to a distal end of which a venous puncture needle is connectable, the blood circuit being capable of extracorporeally circulating blood of a patient; a blood purification device provided between the arterial blood circuit and the venous blood circuit of the blood circuit and being capable of purifying the blood flowing through the blood circuit; a blood pump provided to the arterial blood circuit and being capable of delivering liquid when activated; and a control device that executes a connected step in which the blood pump is activated with the arterial puncture needle and the venous puncture needle being stuck in the patient, and an unconnected step in which the blood pump is activated with neither the arterial puncture needle nor the venous puncture needle being stuck in the patient. The control device is capable of executing, in the unconnected step, a checking step in which whether the arterial puncture needle and/or the venous puncture needle is not stuck in the patient is checked.

According to the teachings herein, in the blood purification apparatus taught herein, in the unconnected step, the control device makes a determination in the checking step by causing the liquid to be delivered from the distal end of the arterial blood circuit or the distal end of the venous blood circuit toward the blood purification device.

According to the teachings herein, the blood purification apparatus taught herein further includes a blood-checking device that is capable of checking presence of blood flowing in at least one of the arterial blood circuit and the venous blood circuit. The determination in the checking step is made on the basis of a result of checking of the presence of blood that is performed by the blood-checking device.

According to the teachings herein, in the blood purification apparatus taught herein, a threshold for the checking of the presence of blood that is performed by the blood-checking device is changed between that for a step performed during the blood purification treatment and that for the checking step.

According to the teachings herein, the blood purification apparatus taught herein further includes a blood-concentration detection device capable of detecting concentration of the blood flowing in at least one of the arterial blood circuit and the venous blood circuit. The determination in the checking step is made on the basis of a value detected by the blood-concentration detection device.

According to the teachings herein, in the blood purification apparatus taught herein, the determination in the checking step is made on the basis of over-time changes in the value detected by the blood-concentration detection device.

According to the teachings herein, in the blood purification apparatus taught herein, the venous blood circuit is provided with a venous air-trap chamber, wherein venous pressure is detectable on the basis of liquid pressure in the venous air-trap chamber. Furthermore, the determination in the checking step is made on the basis of the venous pressure.

According to the teachings herein, in the blood purification taught herein, the control device executes the checking step only at the activation of the blood pump after transition from the connected step to the unconnected step.

According to the teachings herein, the blood purification apparatus according to the teachings herein further includes a dialysate introduction line through which dialysate is introduced into the blood purification device, and a dialysate drain line through which drain liquid is discharged from the blood purification device. The unconnected step is a draining step in which the liquid in the blood circuit is discharged into the dialysate drain line after a blood purification treatment performed by the blood purification device or a returning step.

According to the teachings herein, the control device is capable of executing, in the unconnected step, the checking step in which whether the arterial puncture needle and/or the venous puncture needle is not stuck in the patient is checked. Hence, when it is attempted to activate the blood pump in the unconnected step, the fact that neither the arterial puncture needle nor the venous puncture needle is stuck in the patient can be confirmed automatically.

According to the teachings herein, in the unconnected step, the control device makes the determination in the checking step by causing the liquid to be delivered from the distal end of the arterial blood circuit or the distal end of the venous blood circuit toward the blood purification device. Hence, when it is attempted to activate the blood pump in the unconnected step, the fact that neither the arterial puncture needle nor the venous puncture needle is stuck in the patient can be confirmed more assuredly.

According to the teachings herein, the blood purification apparatus further includes the blood-checking device that is capable of checking the presence of blood flowing in at least one of the arterial blood circuit and the venous blood circuit. Furthermore, the determination in the checking step is made on the basis of the result of the checking of the presence of blood that is performed by the blood-checking device. Hence, the checking step can be performed by utilizing the blood-checking device capable of checking the presence of blood during the blood purification treatment.

According to the teachings herein, the threshold for the checking of the presence of blood that is performed by the blood-checking device is changed between that for the step performed during the blood purification treatment and that for the checking step. Hence, the determination in the checking step using the blood-checking device can be made more accurately.

According to the teachings herein, the blood purification apparatus further includes the blood-concentration detection device capable of detecting the concentration of the blood flowing in at least one of the arterial blood circuit and the venous blood circuit. Furthermore, the determination in the checking step is made on the basis of the value detected by the blood-concentration detection device. Hence, the checking step can be performed by utilizing the blood-concentration detection device that is capable of detecting the blood concentration during the blood purification treatment.

According to the teachings herein, the determination in the checking step is made on the basis of over-time changes in the value detected by the blood-concentration detection device. Hence, the determination in the checking step using the blood-concentration detection device can be made more accurately.

According to the teachings herein, the venous blood circuit is provided with the venous air-trap chamber. Furthermore, the venous pressure is detectable on the basis of liquid pressure in the venous air-trap chamber. Furthermore, the determination in the checking step is made on the basis of the venous pressure. Hence, the checking step can be performed by utilizing the venous pressure detected during the blood purification treatment.

According to the teachings herein, the control device executes the checking step only at the activation of the blood pump after the transition from the connected step to the unconnected step. Hence, among a plurality of unconnected steps, only those with high probability that the arterial puncture needle or the venous puncture needle may be kept being stuck in the patient are allowed to be put to the checking step.

According to the teachings herein, the blood purification apparatus further includes the dialysate introduction line through which the dialysate is introduced into the blood purification device, and the dialysate drain line through which the drain liquid is discharged from the blood purification device. Furthermore, the unconnected step is the draining step in which the liquid in the blood circuit is discharged into the dialysate drain line after the blood purification treatment performed by the blood purification device or the returning step. Hence, when it is attempted to activate the blood pump in the draining step, the fact that the arterial puncture needle or the venous puncture needle is stuck in the patient can be notified more assuredly.

DETAILED DESCRIPTION

An embodiment of the present teachings will now be described specifically with reference to the drawings.

Figure 1:
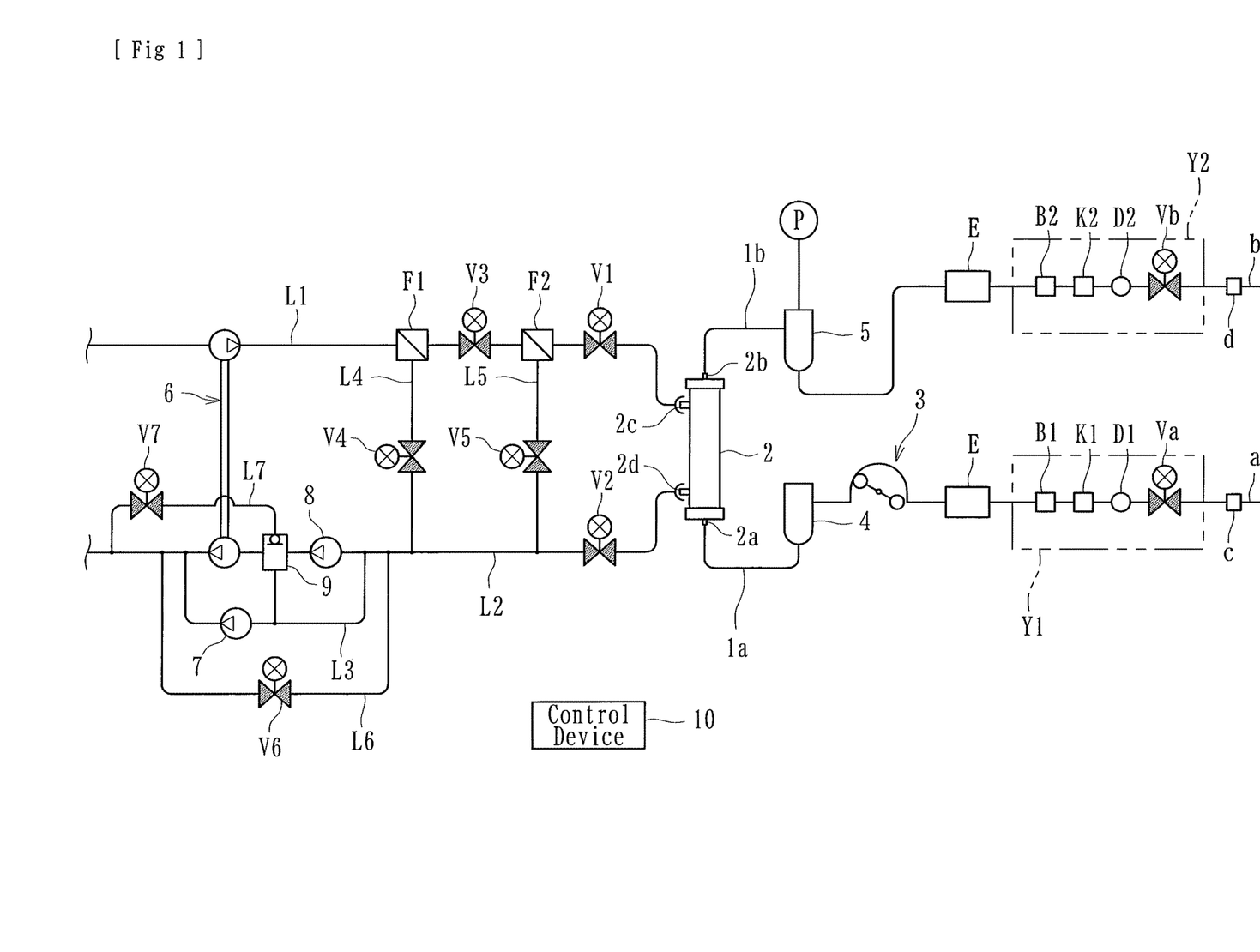
FIG. 1 is a schematic diagram of a blood purification apparatus according to an embodiment of the present teachings.

A blood purification apparatus according to the present embodiment is a dialysis apparatus for giving a dialysis treatment and includes, as illustrated in FIG. 1, a blood circuit 1 including an arterial blood circuit 1a and a venous blood circuit 1b, a dialyzer 2 (a blood purification device) provided between the arterial blood circuit 1a and the venous blood circuit 1b and that purifies blood flowing in the blood circuit 1, a blood pump 3 provided to the arterial blood circuit 1a and that is capable of delivering liquid when activated, an arterial air-trap chamber 4 connected to the arterial blood circuit 1a, a venous air-trap chamber 5 connected to the venous blood circuit 1b, a dialysate introduction line L1 through which dialysate is introduced into the dialyzer 2, a dialysate drain line L2 through which drain liquid is discharged from the dialyzer 2, and a control device 10.

The arterial blood circuit 1a is provided at the distal end thereof with a connector c to which an arterial puncture needle a is connectable. The blood pump 3, which is of a peristaltic type, and the arterial air-trap chamber 4 are provided at respective halfway positions of the arterial blood circuit 1a. On the other hand, the venous blood circuit 1b is provided at the distal end thereof with a connector d to which a venous puncture needle b is connectable. The venous air-trap chamber 5 is provided at a halfway position of the venous blood circuit 1b.

When the blood pump 3 is activated with the arterial puncture needle (a) at the distal end of the arterial blood circuit 1a and the venous puncture needle (b) at the distal end of the venous blood circuit 1b being stuck in the patient, blood of the patient flows through the arterial blood circuit 1a while undergoing bubble removal (air bubbles are removed) in the arterial air-trap chamber 4 and reaches the dialyzer 2, where the blood is purified. Then, the blood flows through the venous blood circuit 1b while undergoing bubble removal (air bubbles are removed) in the venous air-trap chamber 5 and returns into the body of the patient. Thus, the blood of the patient can be purified by the dialyzer 2 while being extracorporeally circulated through the blood circuit 1 from the distal end of the arterial blood circuit 1a to the distal end of the venous blood circuit 1b.

The venous air-trap chamber 5 is provided with a venous pressure sensor P that is capable of detecting venous pressure on the basis of liquid pressure in the venous blood circuit 1b. The venous pressure sensor P is electrically connected to the control device 10 and is capable of outputting a detected value. Thus, the venous pressure of the blood that is under extracorporeal circulation through the blood circuit 1 can be monitored, and changes in the condition of the patient who is taking a treatment can be notified.

The dialyzer 2 has, in a housing thereof, a blood inlet 2a (a blood introduction port), a blood outlet 2b (a blood delivery port), a dialysate inlet 2c (an inlet of the dialysate flow route, or a dialysate introduction port), and a dialysate outlet 2d (an outlet of the dialysate flow route, or a dialysate delivery port). The arterial blood circuit 1a is connected to the blood inlet 2a. The venous blood circuit 1b is connected to the blood outlet 2b. The dialysate inlet 2c and the dialysate outlet 2d are connected to the dialysate introduction line L1 and the dialysate drain line L2, respectively.

The dialyzer 2 houses a plurality of hollow fiber membranes (not illustrated). The hollow fibers serve as blood purification membranes for purifying the blood. The dialyzer 2 has a blood flow route (a flow route between the blood inlet 2a and the blood outlet 2b) in which the blood of the patient flows through the blood purification membranes, and a dialysate flow route (a flow route between the dialysate inlet 2c and the dialysate outlet 2d) in which the dialysate flows. The hollow fiber membranes serving as the blood purification membranes each have a number of very small holes (pores) extending therethrough from the outer peripheral surface to the inner peripheral surface, whereby the hollow fiber membranes are provided. Impurities and the like contained in the blood are allowed to flow through the membranes into the dialysate.

The arterial blood circuit 1a and the venous blood circuit 1b according to the present embodiment are each provided at the distal end thereof (near the connector c or the connector d) with an air-bubble detection device (B1 or B2) that is capable of detecting gas (air bubbles) contained in the blood flowing through the arterial blood circuit 1a or the venous blood circuit 1b during the blood purification treatment. As illustrated in FIGS. 5 to 8, the air-bubble detection device (B1 or B2) is provided in a unit (Y1 or Y2) that includes a blood-checking device (K1 or K2) and a clamping device (Va or Vb) (for example, an electromagnetic valve). Reference character R given in the drawings denote a pushrod for closing or opening a flexible tube by energizing the clamping device (Va or Vb).

Figure 5:
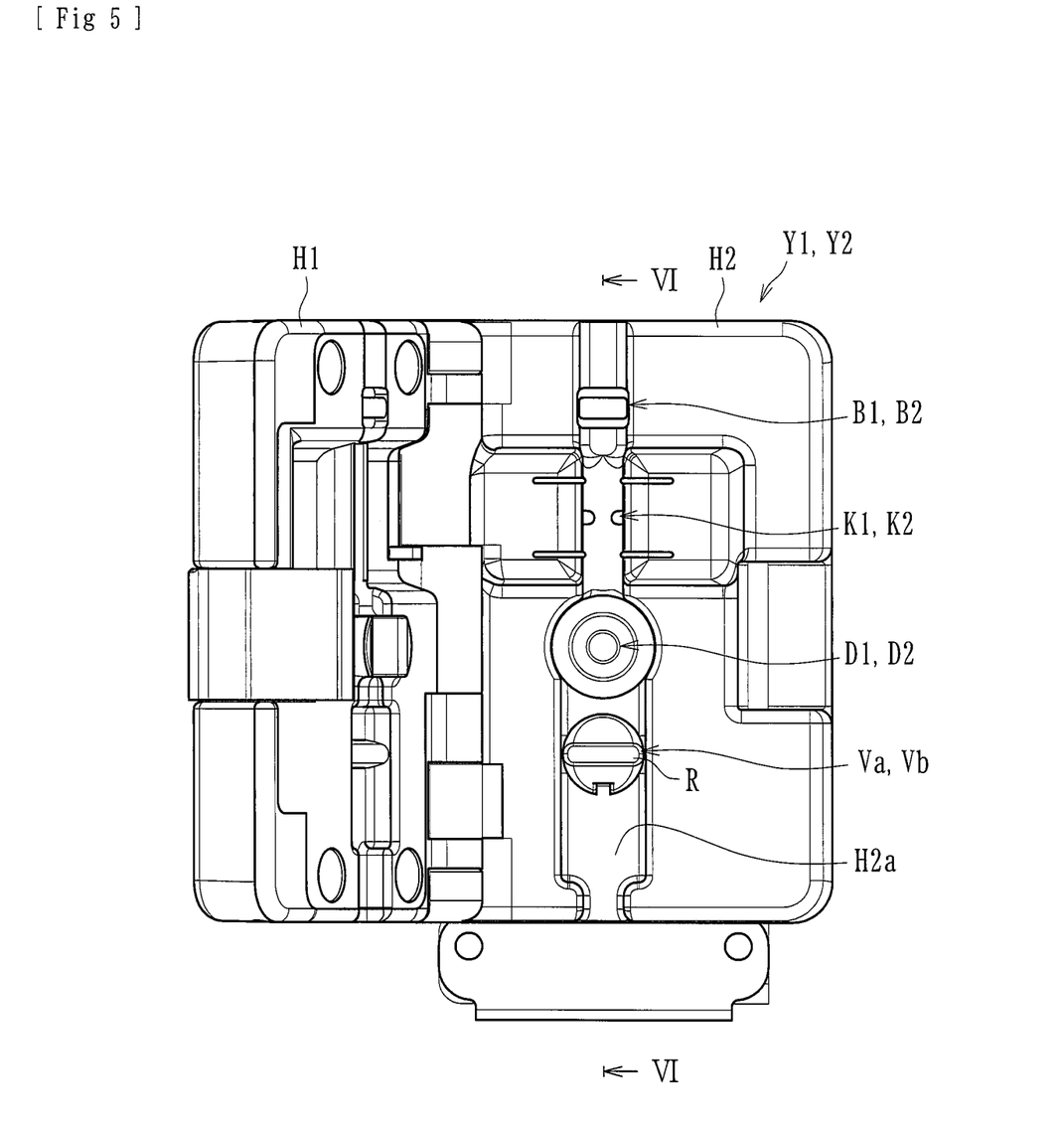
FIG. 5 is a plan view of one of units included in the blood purification apparatus and in each of which an air-bubble detection device and a corresponding one of the blood-checking devices are provided.
Figure 6:
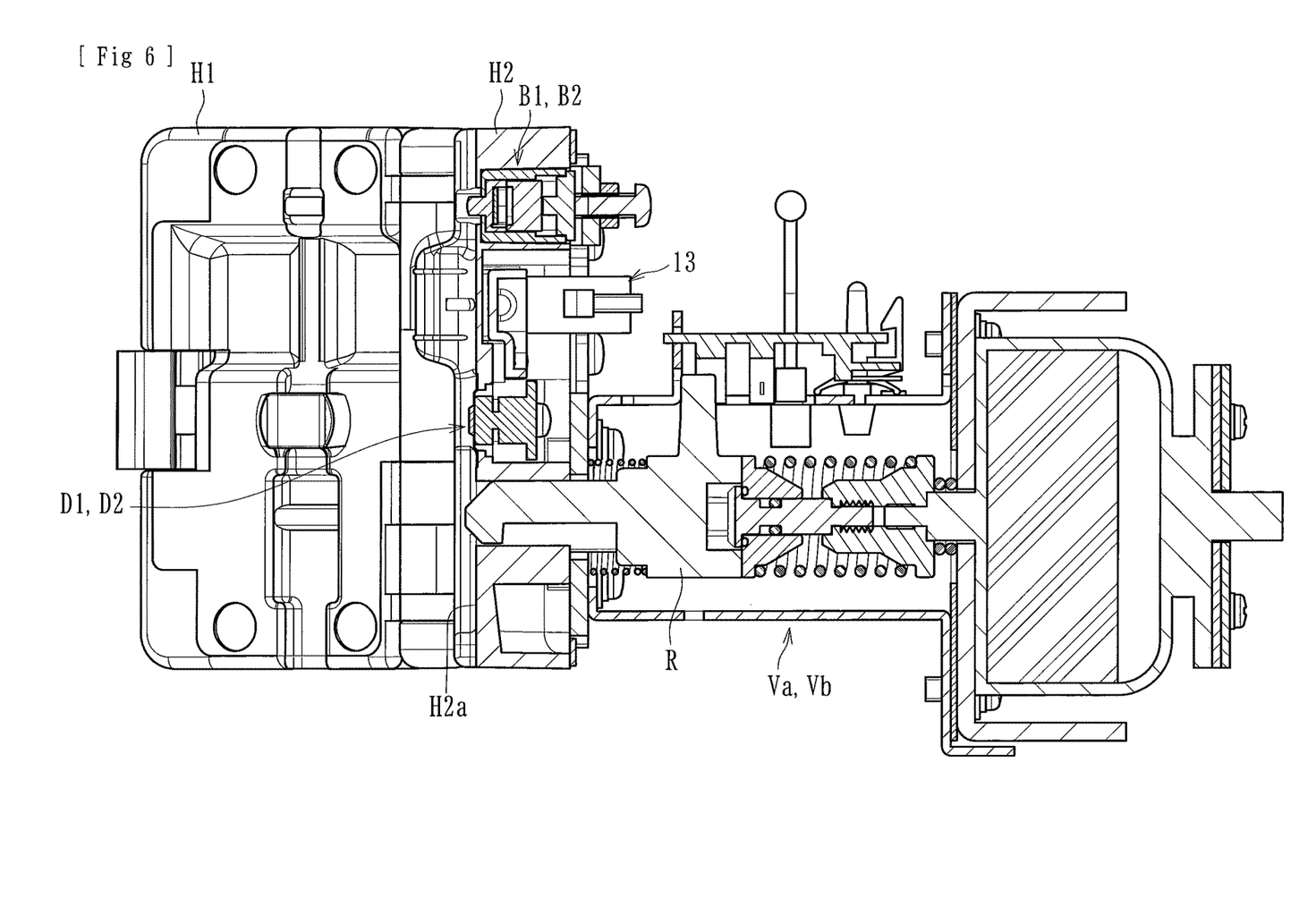
FIG. 6 illustrates a section taken along line VI-VI illustrated in FIG. 5.

The unit (Y1 or Y2) includes a housing, which includes a lid portion H1 and a body portion H2. The unit (Y1 or Y2) has a groove H2a provided in the body portion H2 and includes the air-bubble detection device (B1 or B2), the blood-checking device (K1 or K2), and the clamping device (Va or Vb) that are provided in the body portion H2. The groove H2a can receive a part of the flexible tube forming the arterial blood circuit 1a or the venous blood circuit 1b. The groove H2a communicates, through slits, with a housing space for housing an ultrasonic receiving element α1 and an ultrasonic vibration element α2 that are included in the air-bubble detection device (B1 or B2) and with a housing space for housing a light-emitting element β1 and a light-receiving element β2 that are included in the blood-checking device (K1 or K2).

Figure 7:
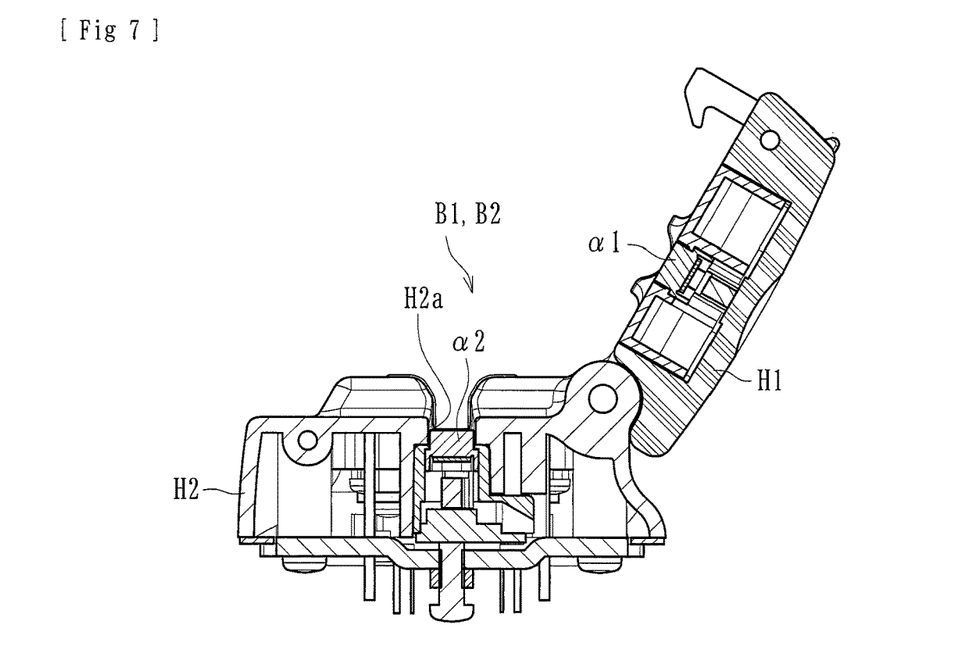
FIG. 7 is a sectional view of the air-bubble detection device provided in the unit.

The air-bubble detection device (B1 or B2) is a sensor capable of detecting bubbles (air) flowing in the flexible tube fitted in the groove H2a. As illustrated in FIG. 7, the air-bubble detection device (B1 or B2) includes, for example, the ultrasonic vibration element α2 formed of a piezoelectric element, and the ultrasonic receiving element α1 formed of a piezoelectric element. The air-bubble detection device (B1 or B2) is capable of emitting ultrasonic waves from the ultrasonic vibration element α2 toward the flexible tube forming the arterial blood circuit 1a or the venous blood circuit 1b fitted in the groove H2a, and is also capable of receiving the thus generated vibration by the ultrasonic receiving element α1. The ultrasonic receiving element α1 is configured such that the voltage changes with the vibration received. The ultrasonic receiving element α1 is capable of detecting the flow of bubbles on the basis of the fact that the detected voltage has exceeded a predetermined threshold. Specifically, since the ultrasonic attenuation factor of bubbles is higher than those of blood and substitution solutions, the fact that the voltage detected by the ultrasonic receiving element α1 has exceeded the predetermined threshold is detected as the flow of bubbles (gas).

Figure 8:
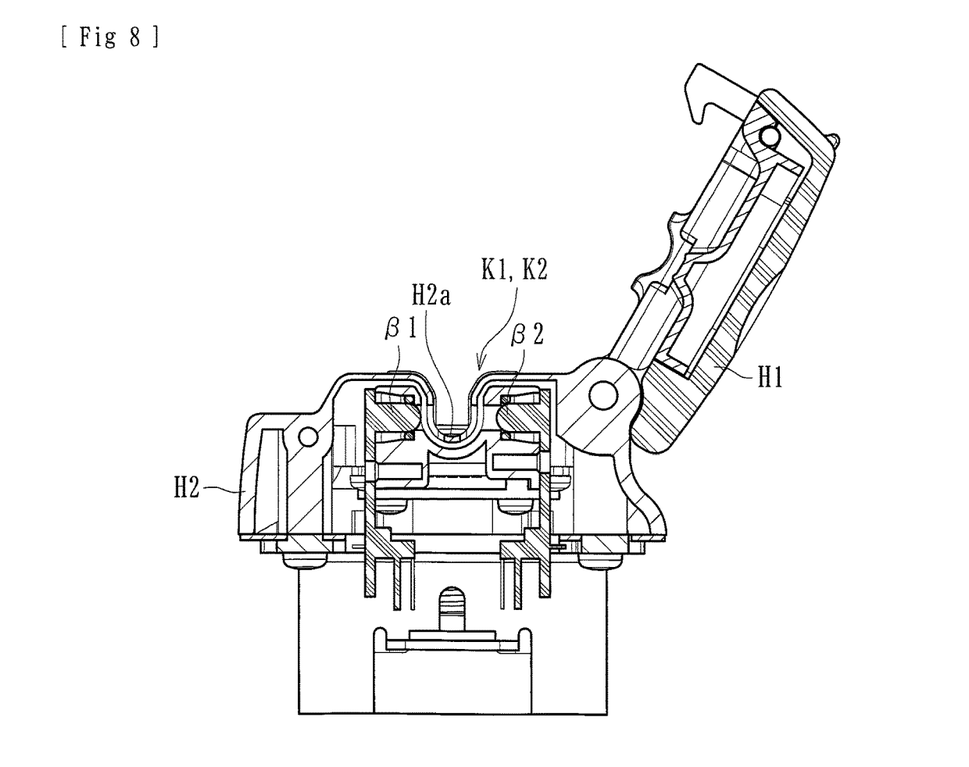
FIG. 8 is a sectional view of the blood-checking device provided in the unit.

The blood-checking device (K1 or K2) is a checking sensor capable of checking whether or not there is any blood flowing in the flexible tube fitted in the groove H2a. As illustrated in FIG. 8, the blood-checking device (K1 or K2) includes, for example, the light-emitting element β1 formed of an LED and the light-receiving element β2. The light-emitting element β1 and the light-receiving element β2 are provided on two respective sides of the groove H2a. The light-emitting element β1 is capable of emitting light toward the flexible tube forming the arterial blood circuit 1a or the venous blood circuit 1b fitted in the groove H2a, and the light-receiving element β2 is capable of receiving the light.

The voltage of the light-receiving element β2 changes with the amount of light received. Hence, whether or not there is any blood flowing in the arterial blood circuit 1a or the venous blood circuit 1b is detectable on the basis of the detected voltage. Specifically, since blood and the substitution solution (the dialysate in the present embodiment) have different levels of transmittance for the light emitted from the light-emitting element β1 (the substitution solution such as a physiological saline solution has a higher light transmittance than blood), the fact that the voltage detected by the light-receiving element β2 has exceeded a predetermined threshold is detected as the fact that the substitution solution as the flowing liquid has been substituted with blood. If the threshold is changed, the blood-checking device (K1 or K2) is also capable of confirming, in a checking step to be described later, the fact that neither the arterial puncture needle a nor the venous puncture needle b is stuck in the patient in an unconnected step.

The unit Y1 or Y2 according to the present embodiment is provided with a detection switch D1 or D2 (see FIG. 1) that is capable of detecting the fact that the lid portion H1 is closed with the flexible tube forming the arterial blood circuit 1a or the venous blood circuit 1b being fitted in the groove H2a. The detection switch D1 or D2 is electrically connected to the control device 10 and is capable of detecting whether or not the blood circuit 1 is set in the air-bubble detection device (B1 or B2) and in the blood-checking device (K1 or K2). The same detection switch is also provided in a blood-concentration detection sensor E to be described later.

The venous blood circuit 1b and the arterial blood circuit 1a according to the present embodiment are each provided with the blood-concentration detection device E that is capable of detecting the concentration of the blood flowing in the blood circuit 1 during the blood purification treatment. The blood-concentration detection device E is a device called hematocrit sensor and is capable of measuring blood concentration on the basis of light-receiving voltage obtained by receiving the reflection of light applied to the blood flowing in the venous blood circuit 1b.

Figure 9:
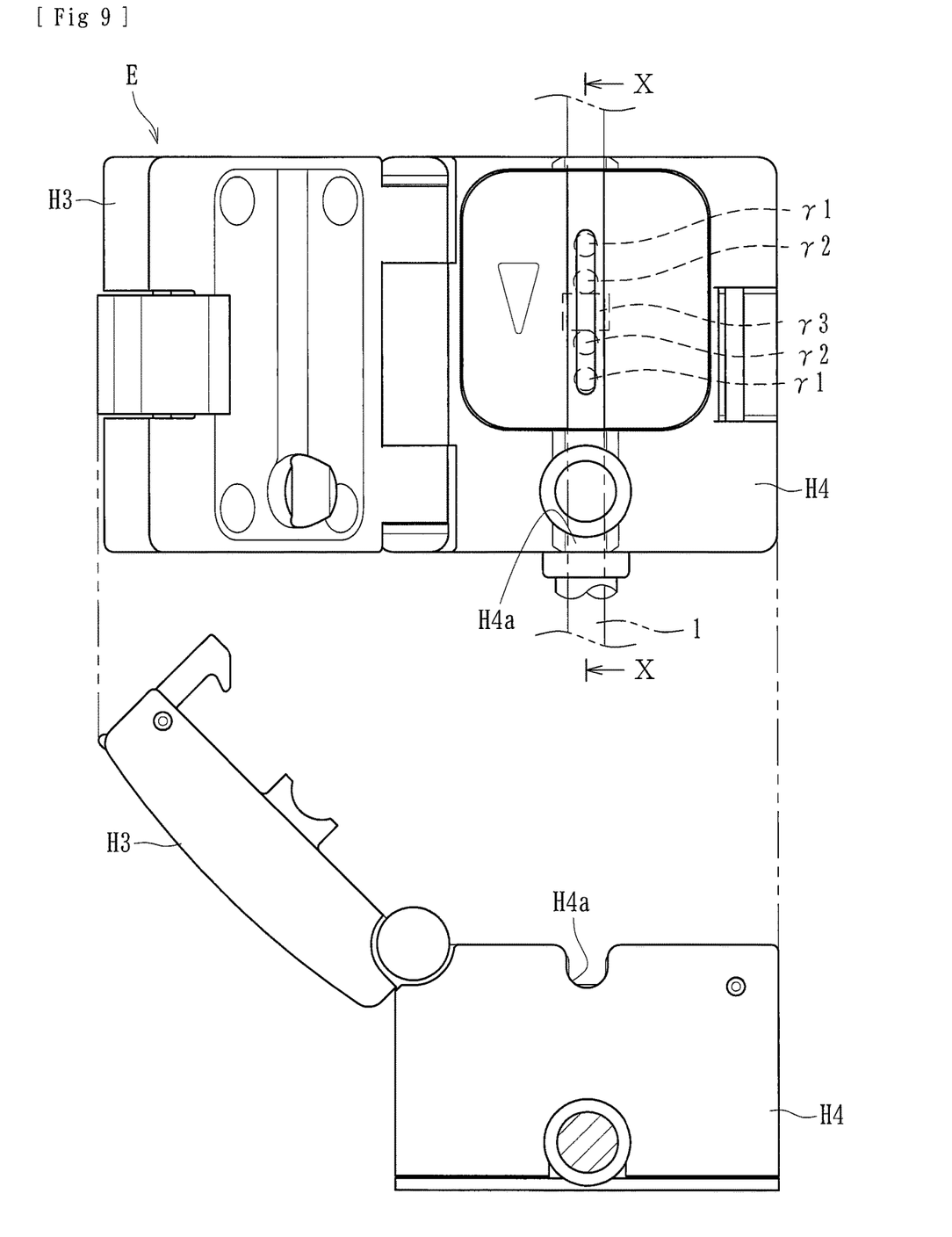
FIG. 9 includes a plan view and a front view of one of the blood-concentration detection devices included in the blood purification apparatus.
Figure 10:
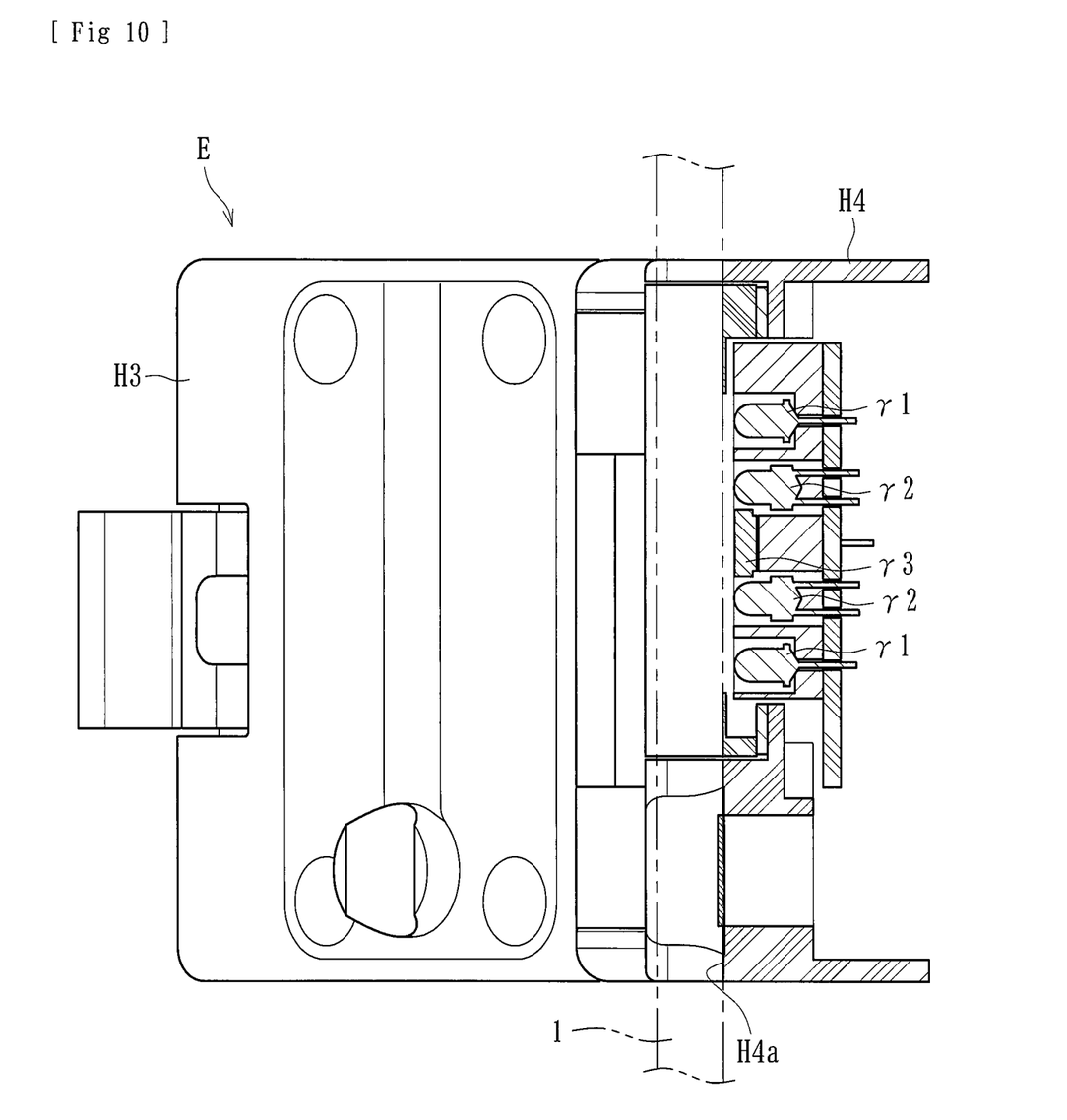
FIG. 10 illustrates a section taken along line X-X illustrated in FIG. 9.

More specifically, as illustrated in FIGS. 9 and 10, the blood-concentration detection device E includes a housing, which includes a lid portion H3 and a body portion H4. The blood-concentration detection device E has a groove H4a provided in the body portion H4 and includes a pair of light-emitting elements γ1 and γ2 and a light-receiving element γ3 that are provided in the body portion H4. The groove H4a can receive a part of the flexible tube forming the venous blood circuit 1b. The groove H4a communicates, through a slit, with a housing spaces for housing the light-emitting elements γ1 and γ2 and the light-receiving element γ3.

The light-emitting elements γ1 and γ2 are each, for example, an LED capable of emitting near-infrared rays (a near-infrared LED). The light-receiving element γ3 is a photodiode. When light is emitted from the light-emitting elements γ1 and γ2 in a state where the body portion H4 is covered by the lid portion H3 with the flexible tube being fitted in the groove H4a, the light travels through the slit, reaches the flexible tube fitted in the groove H4a, is reflected by the blood flowing therein, and is received by the light-receiving element γ3 (a configuration as a so-called reflection sensor).

Then, on the basis of the light-receiving voltage generated by the light-receiving element γ3, the hematocrit value representing the concentration of blood is calculated. Blood components such as red blood cells and blood plasma have respectively specific extinction characteristics. Hence, red blood cells required for measuring the hematocrit value are electro-optically quantified by utilizing such characteristics, whereby the hematocrit value can be obtained. While the blood-concentration detection device E according to the present embodiment is a so-called reflection sensor as described above, the blood-concentration detection device E may be any device that emits light from a light-emitting element and is capable of measuring the hematocrit value (blood concentration) on the basis of the light-receiving voltage obtained by receiving the light transmitted through the blood and received by a light-receiving element.

On the other hand, the dialysate introduction line L1 and the dialysate drain line L2 are provided with a duplex pump 6 that delivers a dialysate prepared to have a predetermined concentration to the dialyzer 2 and discharges waste products and the like (drain liquid) together with the dialysate from the dialyzer 2. Specifically, the duplex pump 6 is provided over the dialysate introduction line L1 and the dialysate drain line L2. When the duplex pump 6 is activated, the dialysate can be introduced into the dialyzer 2 through the dialysate introduction line L1 and be discharged from the dialyzer 2 through the dialysate drain line L2.

The dialysate introduction line L1 is provided with electromagnetic valves V1 and V3 and filtration filters F1 and F2. The dialysate to be introduced into the dialyzer 2 can be filtered by the filtration filters F1 and F2, and the flow route of the dialysate is closable or openable at an arbitrary timing by the electromagnetic valves V1 and V3. The dialysate introduction line L1 is connected to the dialysate drain line L2 with bypass lines L4 and L5. The bypass lines L4 and L5 are provided with electromagnetic valves V4 and V5, respectively.

Furthermore, detour lines L3 and L6 for detouring the duplex pump 6 are connected to the dialysate drain line L2. The detour line L6 is provided with an electromagnetic valve V6. The detour line L3 is provided with an ultrafiltration pump 7. Hence, when the ultrafiltration pump 7 is activated in the process of extracorporeally circulating the blood of the patient through the blood circuit 1, ultrafiltration in which water is removed from the blood flowing through the dialyzer 2 can be performed.

Furthermore, the dialysate drain line L2 is provided with a pressurizing pump 8 at a position thereof on the upstream side (the right side in FIG. 1) with respect to the duplex pump 6. The pressurizing pump 8 adjusts the liquid pressure in the dialysate drain line L2 at the duplex pump 6. A detour line L7 extends from a position of the dialysate drain line L2 between the pressurizing pump 8 and the duplex pump 6, with a degassing chamber 9 interposed therebetween. The dialysate drain line L2 and the detour line L7 branching off therefrom are provided with electromagnetic valves V2 and V7, respectively. Hence, the flow route of the dialysate is closable or openable at an arbitrary timing.

The control device 10 is a microcomputer that is electrically connected to various devices such as actuators and sensors included in the blood purification apparatus. The control device 10 executes connected steps (for example, a treatment step, a returning step, and so forth) in which the blood pump 3 is activated with the arterial puncture needle a and the venous puncture needle b being stuck in the patient and unconnected steps (for example, a priming step, a draining step, and so forth) in which the blood pump 3 is activated with neither the arterial puncture needle a nor the venous puncture needle b being stuck in the patient.

More specifically, the control device 10 is configured to control various devices such as actuators and sensors on the basis of preset steps. Examples of such steps include the priming step (an unconnected step) in which the blood circuit 1 is filled with a priming solution, a blood-purification-treatment step (a connected step) in which blood of the patient is purified by the dialyzer 2 while being extracorporeally circulated through the blood circuit 1, the returning step (a connected step) in which blood of the patient in the blood circuit 1 is returned into the patient, and the draining step (an unconnected step) in which liquid (liquid obtained in the returning step that is a mixture of the substitution solution and a slight amount of blood) in the blood circuit 1 is discharged into the dialysate drain line L2. The control device 10 is capable of controlling the foregoing steps to be performed in the above order. That is, the unconnected steps are each performed on the premise that neither the arterial puncture needle a nor the venous puncture needle b is stuck in the patient, whereas the connected steps are each performed on the premise that the arterial puncture needle a and the venous puncture needle b are stuck in the patient.

The control device 10 according to the present embodiment is configured to execute, in each of the unconnected steps, a checking step in which the fact that neither the arterial puncture needle (a) nor the venous puncture needle (b) is stuck in the patient is checked. Specifically, in the unconnected step, the liquid is delivered to the dialyzer 2 from the distal end of the arterial blood circuit 1a or the distal end of the venous blood circuit 1b, and the checking step is performed (the fact that the arterial puncture needle (a) and/or the venous puncture needle (b) is not stuck in the patient is checked).

After the arterial puncture needle (a) and the venous puncture needle (b) are removed from the patient when the returning step ends, the liquid is delivered from the distal end of the arterial blood circuit 1a or the distal end of the venous blood circuit 1b toward the dialyzer 2. Thus, the liquid remaining in the blood circuit 1 as a mixture of the substitution solution and blood is substituted with air taken from the distal ends of the arterial blood circuit 1a and the venous blood circuit 1b and is discharged from the dialysate drain line L2 through the purification membranes provided in the dialyzer 2. Thus, the draining step can be performed, and the checking step can be performed in the draining step.

The method of delivering the liquid from the distal end of the arterial blood circuit 1a or the distal end of the venous blood circuit 1b toward the dialyzer 2 is arbitrary and may be any of the following examples. In a first method, the electromagnetic valves V2 and V6 are opened so that the relevant flow route is opened, whereas the electromagnetic valve V7 is closed so that the relevant flow route is closed. Furthermore, the pressurizing pump 8 is activated, whereas the duplex pump 6 and the ultrafiltration pump 7 are stopped. In this method, the other electromagnetic valves may be either open or closed, and the pumps other than the duplex pump 6 and the ultrafiltration pump 7 may be in operation.

In a second method, the electromagnetic valves V2 and V7 are opened so that the relevant flow route is opened, whereas the electromagnetic valve V6 is closed so that the relevant flow route is closed. Furthermore, the pressurizing pump 8 is activated, whereas the duplex pump 6 and the ultrafiltration pump 7 are stopped. In this method, the duplex pump 6 and the ultrafiltration pump 7 may be activated, and the other electromagnetic valves are preferably opened or closed in accordance with the respective states of operation of the duplex pump 6 and the ultrafiltration pump 7. In a third method, the electromagnetic valve V2 is opened so that the relevant flow route is opened, whereas the electromagnetic valves V6 and V7 are closed so that the relevant flow route is closed. Furthermore, the pressurizing pump 8 and the ultrafiltration pump 7 are activated, whereas the duplex pump 6 is stopped. In this method, the duplex pump 6 may be activated, and the electromagnetic valves other than the electromagnetic valves V2, V6, and V7 are preferably opened or closed in accordance with the state of operation of the duplex pump 6.

Figure 2:
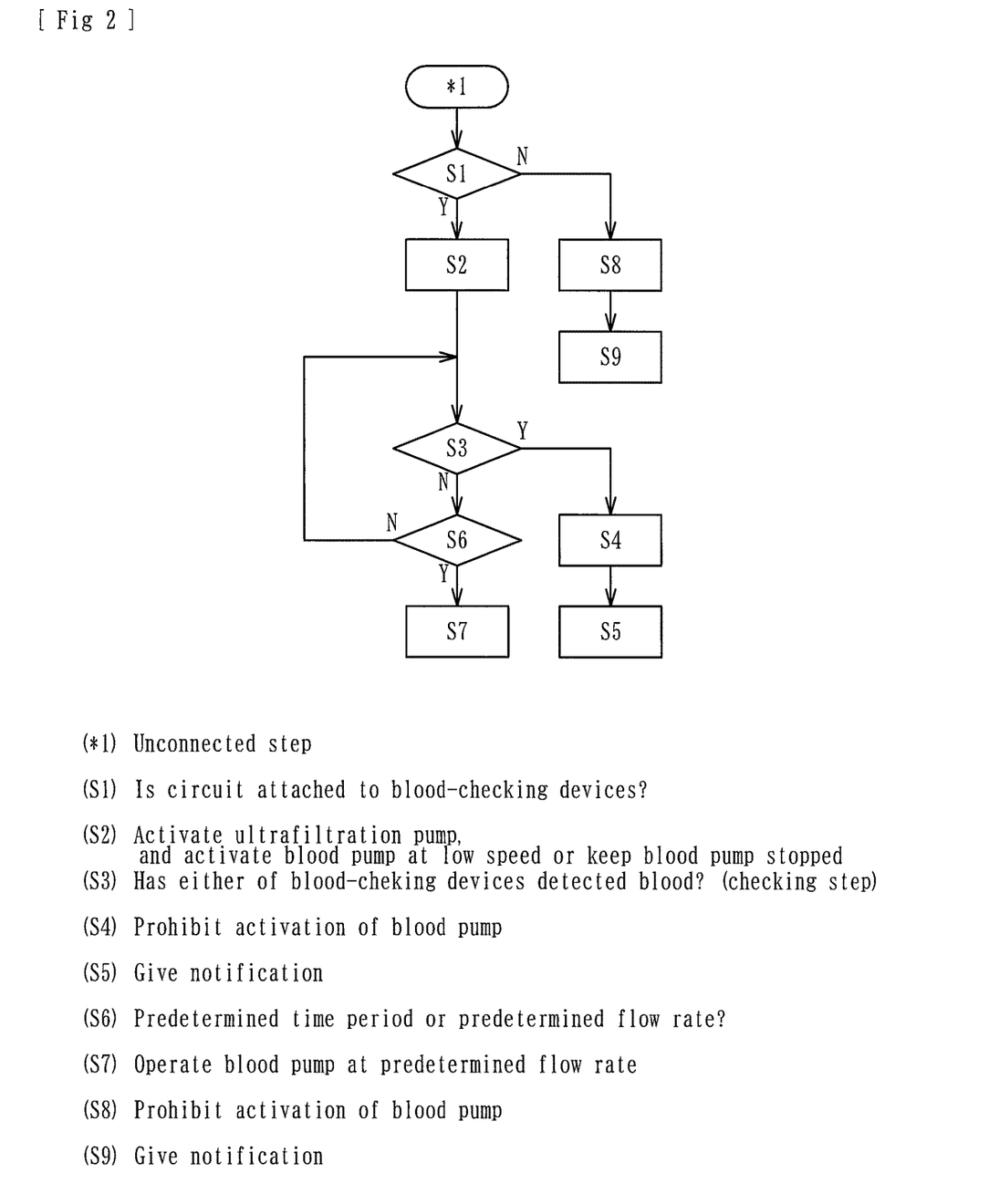
FIG. 2 is a flow chart illustrating a control process for an unconnected step (a control process based on blood-checking devices) that is executed by a control device included in the blood purification apparatus.

Now, a control process for an unconnected step that is executed by the control device 10 (a control process based on the blood-checking device) will be described with reference to the flow chart illustrated in FIG. 2.

First, whether or not the blood circuit 1 is attached to the blood-checking devices (K1 and K2) is checked on the basis of signals from the detection switches D1 and D2 of the units Y1 and Y2 (S1). If it is determined that the blood circuit 1 is not attached, the process proceeds to step S8, where the activation of the blood pump 3 is prohibited. Then, the fact that the blood circuit 1 is not attached to the blood-checking devices (K1 and K2) is notified by, for example, providing an indication on a monitor or the like, generating a warning sound, blinking a warning lamp, or the like (S9).

If it is determined that the blood circuit 1 is attached to the blood-checking devices (K1 and K2) in step S1, the ultrafiltration pump 7 is activated while the blood pump 3 is activated at a low speed or is kept in the stopped state (S2). In this step, to activate the blood pump 3 at a low speed, the flow rate of the blood pump 3 is set to a lower level than the flow rate of the ultrafiltration pump 7. Thus, in the unconnected step, the liquid can be delivered from the distal end of the arterial blood circuit 1a or the distal end of the venous blood circuit 1b toward the dialyzer 2.

Then the process proceeds to step S3, which is the checking step, where whether or not the blood-checking devices (K1 and K2) have identified the presence of blood is checked. If neither of the blood-checking devices (K1 and K2) have identified the presence of blood, it can be determined that neither the arterial puncture needle (a) nor the venous puncture needle (b) is stuck in the patient in the unconnected step. That is, if the blood-checking device K1 has identified the presence of blood, it can be determined that the arterial puncture needle (a) is stuck in the patient. If the blood-checking device K2 has identified the presence of blood, it can be determined that the venous puncture needle (b) is stuck in the patient.

In step S3, if either of the blood-checking devices (K1 and K2) has identified the presence of blood, the process proceeds to step S4, where the activation of the blood pump 3 is prohibited. Then, the fact that the arterial puncture needle (a) or the venous puncture needle (b) is stuck in the patient is notified by, for example, providing an indication on a monitor or the like, generating a warning sound, blinking a warning lamp, or the like (S5). In such a control process, the determination (the confirmation of the fact that neither the arterial puncture needle (a) nor the venous puncture needle (b) is stuck in the patient) is made on the basis of the results of checking of the blood presence performed by the blood-checking devices (K1 and K2). On the other hand, if neither of the blood-checking devices (K1 and K2) have identified the presence of blood, the process proceeds to step S6, where whether or not a predetermined period of time has elapsed since the low-speed activation of the blood pump 3 or whether or not the amount of liquid delivered by the activation of the ultrafiltration pump 7 has reached a predetermined level is checked. If it is determined that the predetermined period of time has elapsed or the predetermined amount has been reached, the blood pump 3 is operated such that the flow rate becomes the predetermined level (S7).

Figure 3:
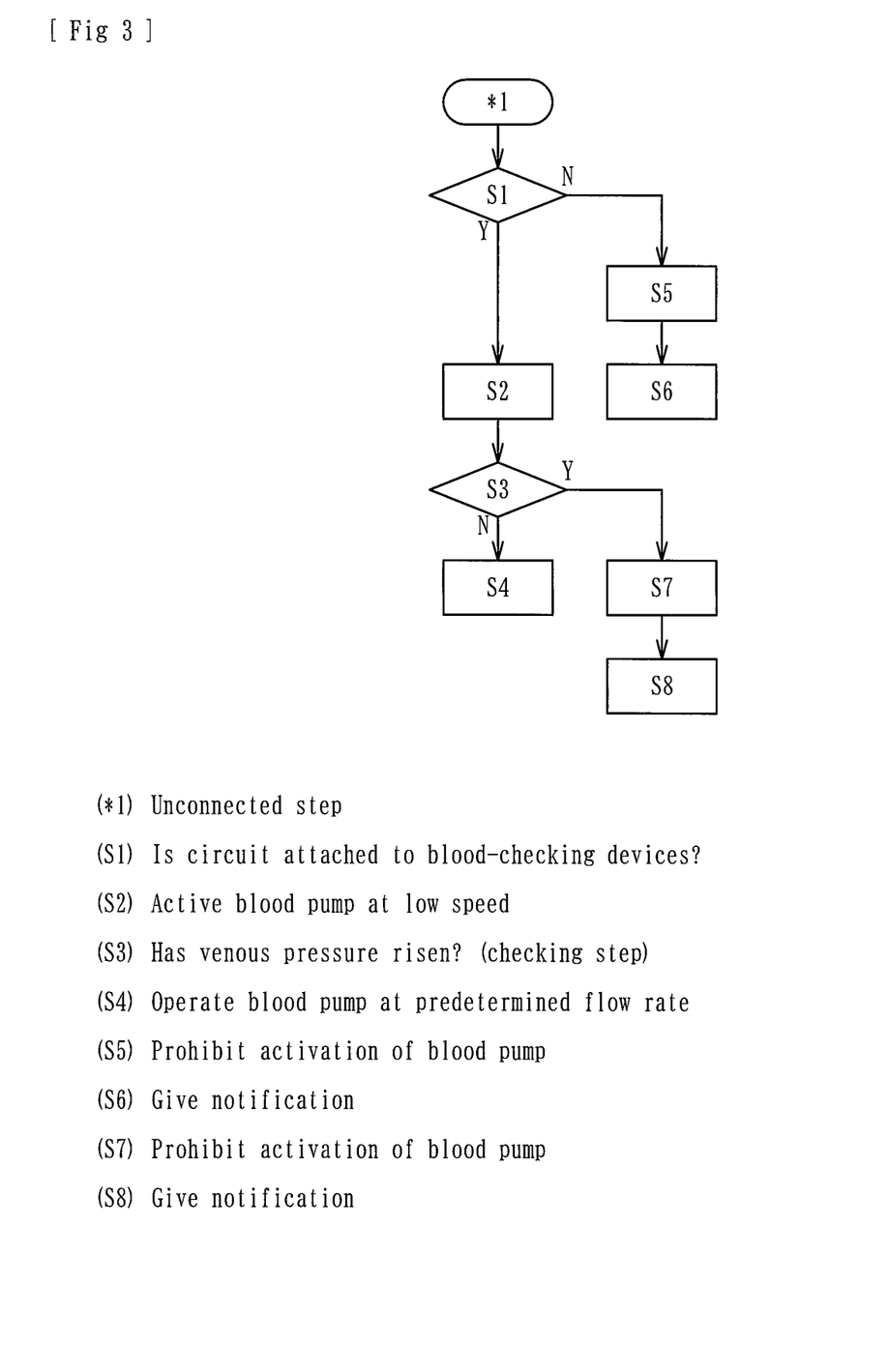
FIG. 3 is a flow chart illustrating another control process for an unconnected step (a control process based on venous pressure) that is executed by the control device included in the blood purification apparatus.

Now, another control process for an unconnected step that is executed by the control device 10 (a control process based on venous pressure) will be described with reference to the flow chart illustrated in FIG. 3.

First, whether or not the blood circuit 1 is attached to the blood-checking devices (K1 and K2) is checked on the basis of signals from the detection switches D1 and D2 of the units Y1 and Y2 (S1). If it is determined that the blood circuit 1 is not attached, the process proceeds to step S5, where the activation of the blood pump 3 is prohibited. Then, the fact that the blood circuit 1 is not attached to the blood-checking devices (K1 and K2) is notified by, for example, providing an indication on a monitor or the like, generating a warning sound, blinking a warning lamp, or the like (S6).

If it is determined that the blood circuit 1 is attached to the blood-checking devices (K1 and K2) in step S1, the process proceeds to step S2, where the blood pump is operated at a low speed (for example, operated at an extremely low speed so that the flow rate becomes 40 mL/min or lower). Then, the process proceeds to step S3, which is the checking step, where whether or not the venous pressure (the value detected by the venous pressure sensor P connected to the venous air-trap chamber 5) has become higher than a predetermined level is checked. If the venous pressure has not become higher than the predetermined level, it can be determined that the venous puncture needle (b) is not stuck in the patient in the unconnected step. If the venous pressure has become higher than the predetermined level, it can be determined that a flow-rate resistance is generated because the venous puncture needle (b) is stuck in the patient. Hence, it can be regarded that at least the venous puncture needle b is stuck in the patient.

If the venous pressure has not become higher than the predetermined level, the blood pump 3 is operated such that the flow rate becomes the predetermined level (S4). If the venous pressure has become higher than the predetermined level, the process proceeds to step S7, where the activation of the blood pump 3 is prohibited. Then, the fact that the arterial puncture needle (a) or the venous puncture needle (b) is stuck in the patient is notified by, for example, providing an indication on a monitor or the like, generating a warning sound, blinking a warning lamp, or the like (S8). In such a control process, the determination (the confirmation of the fact that the venous puncture needle (b) is not stuck in the patient) is made on the basis of the value detected by the venous pressure sensor P connected to the venous air-trap chamber 5.

Figure 4:
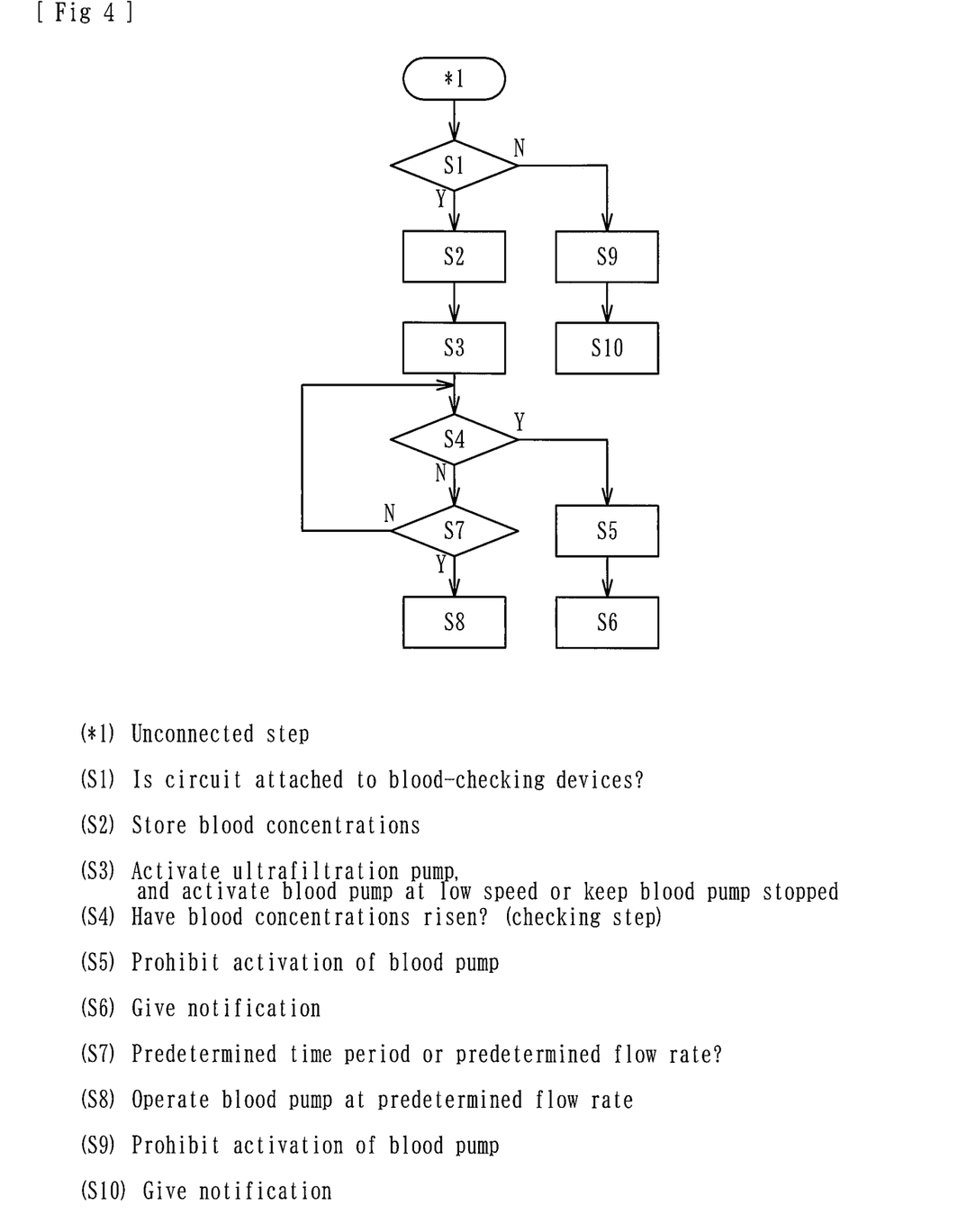
FIG. 4 is a flow chart illustrating yet another control process for an unconnected step (a control process based on blood-concentration detection devices) that is executed by the control device included in the blood purification apparatus.

Now, yet another control process for an unconnected step that is executed by the control device 10 (a control process based on the blood-concentration detection devices E) will be described with reference to the flow chart illustrated in FIG. 4.

First, whether or not the blood circuit 1 is attached to the blood-checking devices (K1 and K2) is checked on the basis of signals from the detection switches D1 and D2 of the units Y1 and Y2 (S1). If it is determined that the blood circuit 1 is not attached, the process proceeds to step S9, where the activation of the blood pump 3 is prohibited. Then, the fact that the blood circuit 1 is not attached to the blood-checking devices (K1 and K2) is notified by, for example, providing an indication on a monitor or the like, generating a warning sound, blinking a warning lamp, or the like (S10).

If it is determined that the blood circuit 1 is attached to the blood-checking devices (K1 and K2) in step S1, the process proceeds to step S2, where the blood concentrations detected by the respective blood-concentration detection devices E are stored. Then, the ultrafiltration pump 7 is activated, and the blood pump 3 is operated at a low speed or is kept in the stopped state (S3). In this step, to activate the blood pump 3 at a low speed, the flow rate of the blood pump 3 is set to a level lower than the flow rate of the ultrafiltration pump 7. Thus, in the unconnected step, the liquid can be delivered from the distal end of the arterial blood circuit 1a or the distal end of the venous blood circuit 1b toward the dialyzer 2.

Then, the process proceeds to step S4, which is the checking step, where whether or not the blood concentrations detected by the blood-concentration detection devices E have become higher than the blood concentrations stored in step S2 is checked. If the blood concentrations have not become higher, it can be determined that neither the arterial puncture needle (a) nor the venous puncture needle (b) is stuck in the patient in the unconnected step. If the blood concentrations have become higher, it can be determined that at least the venous puncture needle (b) is stuck in the patient.

If the blood concentrations have become higher, the process proceeds to step S5, where the activation of the blood pump 3 is prohibited. Then, the fact that at least the venous puncture needle (b) is stuck in the patient is notified by, for example, providing an indication on a monitor or the like, generating a warning sound, blinking a warning lamp, or the like (S6). In such a control process, the determination (the confirmation of the fact that neither the arterial puncture needle (a) nor the venous puncture needle b is stuck in the patient) is made on the basis of over-time changes in the values detected by the blood-concentration detection devices E. On the other hand, if the blood concentrations have not become high, the process proceeds to step S7, where whether or not a predetermined period of time has elapsed since the low-speed activation of the blood pump 3 or whether or not the amount of liquid delivered by the activation of the ultrafiltration pump 7 has reached a predetermined level is checked. If it is determined that the predetermined period of time has elapsed or the predetermined amount has been reached, the blood pump 3 is operated such that the flow rate becomes the predetermined level (S8).

To summarize, in the blood purification apparatus according to the present embodiment, the control device 10 can execute the checking step for confirming that neither the arterial puncture needle a nor the venous puncture needle b is stuck in the patient in the unconnected step. Hence, when it is attempted to activate the blood pump 3 in the unconnected step, the fact that neither the arterial puncture needle a nor the venous puncture needle b is stuck in the patient can be confirmed automatically. In particular, the control device 10 according to the present embodiment executes the checking step in the unconnected step by causing the liquid to be delivered from the distal end of the arterial blood circuit 1a or the distal end of the venous blood circuit 1b toward the dialyzer 2. Hence, when it is attempted to activate the blood pump 3 in the unconnected step, the fact that neither the arterial puncture needle (a) nor the venous puncture needle (b) is stuck in the patient can be confirmed more assuredly.

Furthermore, the blood-checking devices (K1 and K2) each being capable of checking the presence of blood flowing in a corresponding one of the arterial blood circuit 1a and the venous blood circuit 1b included in the blood circuit 1 are provided, and the checking step is executed on the basis of the results of checking of the blood presence performed by the blood-checking devices (K1 and K2). Hence, the checking step can be performed by utilizing the blood-checking devices capable of checking the presence of blood during the blood purification treatment. In such a case, the threshold for checking the presence of blood by the blood-checking devices (K1 and K2) is preferably changed between that for the blood purification treatment and that for the checking step. With such a change in the threshold, the determination in the checking step using the blood-checking devices (K1 and K2) can be made more accurately.

Furthermore, the blood-concentration detection devices E each being capable of detecting the concentration of the blood flowing in a corresponding one of the arterial blood circuit 1a and the venous blood circuit 1b included in the blood circuit 1 are provided, and the checking step is performed on the basis of the values detected by the blood-concentration detection devices E. Hence, the checking step can be performed by utilizing the blood-concentration detection devices E each being capable of detecting the blood concentration during the blood purification treatment. In such a case, the determination in the checking step is preferably made on the basis of over-time changes in the values detected by the blood-concentration detection devices E. With the determination based on the over-time changes in the checking step, the determination in the checking step performed by using the blood-concentration detection devices E can be made more accurately.

Furthermore, the venous pressure is detectable on the basis of the liquid pressure in the venous air-trap chamber 5 connected to the venous blood circuit 1b, and the determination in the checking step is made on the basis of the venous pressure. Hence, the checking step can be performed by utilizing the venous pressure detected during the blood purification treatment. Alternatively, the liquid pressure in the arterial air-trap chamber 4 connected to the arterial blood circuit 1a may be detected, and the determination in the checking step may be made on the basis of the liquid pressure.

The control device 10 according to the present embodiment executes the checking step only at the activation of the blood pump 3 after the transition from a connected step to an unconnected step. Hence, among a plurality of unconnected steps, only those with high probability that the arterial puncture needle (a) or the venous puncture needle (b) may be kept being stuck in the patient (that is, only situations where the removal of the arterial puncture needle a or the venous puncture needle b from the corresponding one of the distal ends of the blood circuit 1 may be forgotten) are allowed to be put to the checking step.

Furthermore, the dialysate introduction line L1 through which the dialysate is introduced into the dialyzer 2 and the dialysate drain line L2 through which the drain liquid is discharged from the dialyzer 2 are provided. In addition, the unconnected steps include the draining step in which the liquid in the blood circuit 1 is discharged into the dialysate drain line L2 after the blood purification treatment is performed with the dialyzer 2 or the returning step is performed. Hence, when it is attempted to activate the blood pump 3 in the draining step, the fact that the arterial puncture needle a or the venous puncture needle b is stuck in the patient can be notified more assuredly.

While an embodiment has been described above, the present teachings are not limited thereto. For example, in step S2 in FIG. 2, in step S2 in FIG. 3, and in step S3 in FIG. 4, the blood pump 3 may be operated such that the flow rate becomes a predetermined level. Furthermore, while the above embodiment concerns a case where the unconnected step in which the checking step is to be performed is the draining step, the checking step may be performed in any of the other unconnected steps. While the above embodiment is applied to a dialysis apparatus used in hemodialysis treatment, the present teachings may be applied to any other apparatus that is capable of purifying the blood of the patient while extracorporeally circulating the blood (for example, any of a blood purification apparatus, a blood-plasma-absorbing apparatus, and the like that are used in a hemodiafiltration method, a hemofiltration method, and AFBF).

The control device is applicable to any blood purification apparatus having another function or the like, as long as the apparatus can execute a checking step in which whether an arterial puncture needle and/or a venous puncture needle is not stuck in the patient in each unconnected step can be checked.

REFERENCE SIGN LIST

1 blood circuit
2 dialyzer (blood purification device)
3 blood pump
4 arterial air-trap chamber
5 venous air-trap chamber
6 duplex pump
7 ultrafiltration pump
8 pressurizing pump
9 degassing chamber
10 control device
P venous pressure sensor
K1, K2 blood-checking device
B1, B2 air-bubble detection device
E blood-concentration detection device
L1 dialysate introduction line
L2 dialysate drain line

The invention claimed is:

1. A blood purification apparatus comprising:
a blood circuit including an arterial blood circuit to a distal end of which an arterial puncture needle is connectable, and a venous blood circuit to a distal end of which a venous puncture needle is connectable, the blood circuit being capable of extracorporeally circulating blood of a patient;
a blood purification device provided between the arterial blood circuit and the venous blood circuit of the blood circuit and being capable of purifying the blood flowing through the blood circuit;
a blood pump provided to the arterial blood circuit and being capable of delivering liquid when activated;
a control device that executes a connected step in which the blood pump is activated with the arterial puncture needle and the venous puncture needle being stuck in the patient, and an unconnected step in which the blood pump is activated with neither the arterial puncture needle nor the venous puncture needle being stuck in the patient;

a blood-checking device that checks for a presence of blood flowing in at least one of the arterial blood circuit and the venous blood circuit, wherein a determination in a checking step is made on a basis of a result of checking of the presence of blood that is performed by the blood-checking device; and an air-bubble detection device, a blood-checking device located between the air-bubble detection device and the arterial puncture needle, and a clamping device located between the air-bubble detection device and the arterial puncture needle in the arterial blood circuit;

wherein the blood circuit comprises a detection switch located between the clamping device and the air-bubble detection device;

wherein the control device executes, in the unconnected step, a checking step in which whether the arterial puncture needle and/or the venous puncture needle is not stuck in the patient is checked; and wherein, in the unconnected step, the control device makes a determination in the checking step by causing the liquid to be delivered from the distal end of the arterial blood circuit or the distal end of the venous blood circuit toward the blood purification device.

2. The blood purification apparatus according to claim 1, wherein a threshold for the checking of the presence of blood that is performed by the blood-checking device is changed between that for a step performed during the blood purification treatment and that for the checking step.

3. The blood purification apparatus according to claim 2, wherein the control device executes the checking step only at the activation of the blood pump after transition from the connected step to the unconnected step.

4. The blood purification apparatus according to claim 3, further comprising: a dialysate introduction line through which dialysate is introduced into the blood purification device; and a dialysate drain line through which drain liquid is discharged from the blood purification device, wherein the unconnected step is a draining step in which the liquid in the blood circuit is discharged into the dialysate drain line after a blood purification treatment performed by the blood purification device or a returning step.

5. The blood purification apparatus according to claim 1, wherein the control device executes the checking step only at the activation of the blood pump after transition from the connected step to the unconnected step.

6. The blood purification apparatus according to claim 1, further comprising: a dialysate introduction line through which dialysate is introduced into the blood purification device; and a dialysate drain line through which drain liquid is discharged from the blood purification device, wherein the unconnected step is a draining step in which the liquid in the blood circuit is discharged into the dialysate drain line after a blood purification treatment performed by the blood purification device or a returning step.

7. The blood purification apparatus according to claim 6, wherein the dialysate introduction line comprises electromagnetic valves and filtration filters so that the dialysate to be introduced into a dialyzer is filtered by the filtration filters and a flow route of the dialysate to the dialyzer is openable and closeable by the electromagnetic valves.

8. The blood purification apparatus according to claim 1, wherein the control device executes the checking step only at the activation of the blood pump after transition from the connected step to the unconnected step.

9. The blood purification apparatus according to claim 1, wherein the control device is a microcomputer that is electrically connected to sensors and actuators in the blood purification apparatus.

10. The blood purification apparatus according to claim 1, wherein the arterial blood circuit and the venous blood circuit each include a unit that comprises:
 a housing comprising:
  a body portion;
  a lid portion; and
  a groove in the body portion;
 the air-bubble detection device comprising an ultrasonic receiving element and an ultrasonic vibration element; and
 a blood-checking device comprising a light-receiving element and a light emitting element; and
 wherein the housing includes slits and a housing space that houses the air-bubble detection device and the air-bubble detection device is in communication with the groove through the slits.

11. A blood purification apparatus comprising:
 a blood circuit including an arterial blood circuit to a distal end of which an arterial puncture needle is connectable, and a venous blood circuit to a distal end of which a venous puncture needle is connectable, the blood circuit being capable of extracorporeally circulating blood of a patient;
 a blood purification device provided between the arterial blood circuit and the venous blood circuit of the blood circuit and being capable of purifying the blood flowing through the blood circuit;
 a blood pump provided to the arterial blood circuit and being capable of delivering liquid when activated;
 a control device that executes a connected step in which the blood pump is activated with the arterial puncture needle and the venous puncture needle being stuck in the patient, and an unconnected step in which the blood pump is activated with neither the arterial puncture needle nor the venous puncture needle being stuck in the patient, and
 a blood-concentration detection device that detects concentration of the blood flowing in at least one of the arterial blood circuit and the venous blood circuit, wherein a determination in a checking step is made on a basis of a value detected by the blood-concentration detection device;
 an air-bubble detection device, a blood-checking device located between the air-bubble detection device and the arterial puncture needle, and a clamping device located between the air-bubble detection device and the arterial puncture needle in the arterial blood circuit;
 wherein the blood circuit comprises a detection switch located between the clamping device and the air-bubble detection device;
 wherein the control device executes, in the unconnected step, a checking step in which whether the arterial puncture needle and/or the venous puncture needle is not stuck in the patient is checked; and
 wherein, in the unconnected step, the control device makes a determination in the checking step by causing the liquid to be delivered from the distal end of the arterial blood circuit or the distal end of the venous blood circuit toward the blood purification device.

12. The blood purification apparatus according to claim 11, wherein the determination in the checking step is made on a basis of over-time changes in the value detected by the blood-concentration detection device.

13. The blood purification apparatus according to claim 11, wherein the control device executes the checking step only at the activation of the blood pump after transition from the connected step to the unconnected step.

14. The blood purification apparatus according to claim 11, further comprising: a dialysate introduction line through which dialysate is introduced into the blood purification device; and a dialysate drain line through which drain liquid is discharged from the blood purification device, wherein the unconnected step is a draining step in which the liquid in the blood circuit is discharged into the dialysate drain line after a blood purification treatment performed by the blood purification device or a returning step.

15. The blood purification apparatus according to claim 11, wherein the arterial blood circuit comprises an air-bubble detection device, a blood-checking device located between the air-bubble detection device and the arterial puncture needle, and a clamping device located between the air-bubble detection device and the arterial puncture needle, and wherein the blood circuit comprises a detection switch located between the clamping device and the air-bubble detection device.

16. The blood purification apparatus according to claim 11, wherein the arterial blood circuit and the venous blood circuit each include a unit that comprises:
   a housing comprising:
      a body portion;
      a lid portion; and
      a groove in the body portion;
   the air-bubble detection device comprising an ultrasonic receiving element and an ultrasonic vibration element; and
   a blood-checking device comprising a light-receiving element and a light emitting element; and
   wherein the housing includes slits and a housing space that houses the air-bubble detection device and the air-bubble detection device is in communication with the groove through the slits.

17. A blood purification apparatus comprising:
   a blood circuit including an arterial blood circuit to a distal end of which an arterial puncture needle is connectable, and a venous blood circuit to a distal end of which a venous puncture needle is connectable, the blood circuit being capable of extracorporeally circulating blood of a patient;
   a blood purification device provided between the arterial blood circuit and the venous blood circuit of the blood circuit and being capable of purifying the blood flowing through the blood circuit;
   a blood pump provided to the arterial blood circuit and being capable of delivering liquid when activated;
   a control device that executes a connected step in which the blood pump is activated with the arterial puncture needle and the venous puncture needle being stuck in the patient, and an unconnected step in which the blood pump is activated with neither the arterial puncture needle nor the venous puncture needle being stuck in the patient, and an air-bubble detection device, a blood-checking device located between the air-bubble detection device and the arterial puncture needle, and a clamping device located between the air-bubble detection device and the arterial puncture needle in the arterial blood circuit;
   wherein the blood circuit comprises a detection switch located between the clamping device and the air-bubble detection device;
   wherein the control device executes, in the unconnected step, a checking step in which whether the arterial puncture needle and/or the venous puncture needle is not stuck in the patient is checked;
   wherein, in the unconnected step, the control device makes a determination in the checking step by causing the liquid to be delivered from the distal end of the arterial blood circuit or the distal end of the venous blood circuit toward the blood purification device; and
   wherein the venous blood circuit is provided with a venous air-trap chamber, wherein venous pressure is detected on a basis of liquid pressure in the venous air-trap chamber, and wherein the determination in the checking step is made on a basis of the venous pressure.

18. The blood purification apparatus according to claim 17, further comprising: a dialysate introduction line through which dialysate is introduced into the blood purification device; and a dialysate drain line through which drain liquid is discharged from the blood purification device, wherein the unconnected step is a draining step in which the liquid in the blood circuit is discharged into the dialysate drain line after a blood purification treatment performed by the blood purification device or a returning step.

19. The blood purification apparatus according to claim 17, wherein the arterial blood circuit comprises an air-bubble detection device, a blood-checking device located between the air-bubble detection device and the arterial puncture needle, and a clamping device located between the air-bubble detection device and the arterial puncture needle, and wherein the blood circuit comprises a detection switch located between the clamping device and the air-bubble detection device.

20. The blood purification apparatus according to claim 17, wherein the arterial blood circuit and the venous blood circuit each include a unit that comprises:
   a housing comprising:
      a body portion;
      a lid portion; and
      a groove in the body portion;
   the air-bubble detection device comprising an ultrasonic receiving element and an ultrasonic vibration element; and
   a blood-checking device comprising a light-receiving element and a light emitting element; and
   wherein the housing includes slits and a housing space that houses the air-bubble detection device and the air-bubble detection device is in communication with the groove through the slits.

* * * * *